United States Patent [19]

Hardtmann

[11] 4,273,930
[45] Jun. 16, 1981

[54] 4-HYDROXY-2-QUINOLINONE-3-CARBOXYLIC ACID ESTERS

[75] Inventor: Goetz E. Hardtmann, Morristown, N.J.

[73] Assignee: Sandoz, Inc., E. Hanover, N.J.

[21] Appl. No.: 65,278

[22] Filed: Aug. 9, 1979

Related U.S. Application Data

[60] Division of Ser. No. 807,898, Jun. 20, 1977, Pat. No. 4,190,659, which is a continuation-in-part of Ser. No. 662,148, Feb. 27, 1976, abandoned, which is a continuation-in-part of Ser. No. 557,984, Mar. 12, 1975, abandoned, which is a division of Ser. No. 454,070, Mar. 25, 1974, abandoned, which is a continuation-in-part of Ser. No. 303,099, Nov. 2, 1972, abandoned, and Ser. No. 392,082, Aug. 27, 1973, abandoned.

[51] Int. Cl.³ ............... C07D 215/56; C07D 491/04
[52] U.S. Cl. ................................. 546/90; 546/155; 546/156; 424/258
[58] Field of Search .................. 546/90, 156, 155

[56] References Cited

U.S. PATENT DOCUMENTS

| | | | |
|---|---|---|---|
| 3,287,458 | 11/1966 | Kaminsky et al. | 546/90 |
| 3,506,667 | 4/1970 | Kaminsky | 546/156 |
| 3,509,257 | 4/1970 | Kaminsky et al. | 546/90 |
| 3,524,858 | 8/1970 | Kaminsky et al. | 546/90 |
| 3,542,851 | 11/1970 | Patchett et al. | 546/155 |
| 3,590,036 | 6/1971 | Lesher et al. | 424/263 |
| 3,761,592 | 9/1973 | Mizzoni et al. | 546/155 |
| 3,772,301 | 11/1973 | von Strandtmann et al. | 546/155 |
| 3,853,864 | 12/1974 | Santilli et al. | 424/266 |
| 3,960,868 | 6/1976 | Ferrini et al. | 546/156 |
| 3,963,736 | 6/1976 | Nakagome et al. | 424/255 |
| 3,966,743 | 6/1976 | Berger et al. | 424/258 |
| 4,006,237 | 2/1977 | Buckle et al. | 546/155 |
| 4,036,962 | 7/1977 | Lee | 546/90 |
| 4,107,310 | 8/1978 | Allais et al. | 546/155 |
| 4,117,136 | 9/1978 | Hisada et al. | 546/90 |
| 4,119,720 | 10/1978 | Hardtmann | 546/90 |
| 4,124,587 | 11/1978 | Hardtmann | 546/90 |
| 4,190,659 | 2/1980 | Hardtmann | 424/258 |
| 4,192,876 | 3/1980 | Hardtmann | 546/90 |
| 4,216,324 | 8/1980 | Lee | 546/90 |

FOREIGN PATENT DOCUMENTS

| | | | |
|---|---|---|---|
| 806848 | 10/1973 | Belgium | 546/156 |
| 2431584 | 1/1975 | Fed. Rep. of Germany | 546/156 |
| 2705446 | 8/1977 | Fed. Rep. of Germany | 546/155 |
| 2554772 | 3/1978 | Fed. Rep. of Germany | 546/155 |
| 43-23948 | 10/1968 | Japan | 546/156 |
| 1121411 | 7/1968 | United Kingdom | 546/156 |
| 1334705 | 10/1973 | United Kingdom | 546/156 |

OTHER PUBLICATIONS

Tomita; J., Pharm. Soc. of Japan vol. 71, pp. 1100–1112 (1951).
Buckle et al.; J. Med. Chem. vol. 18, pp. 726–732 (1975).
Ukita et al.; Chem. J. Pharm. Bull., Tokyo vol. 8, pp. 1016–1020 (1960).
Mitschet et al.; Heterocycles, vol. 3, pp. 913–919, (1975).
Anet et al.; Chem. Constituents of Australian Flindersia Species; pp. 412–419, (1951).
Grundon et al.; J. Chem. Soc., pp. 4284–4290, (1955).
Asahina et al.; Berichleder Deutschen Chemischen Gessellschaft; vol. 63, p. 2052, (1930).
McCorkindale; Tetrahedron, vol. 14, pp. 223–229, (1961).
Couhs et al.; J. Chem. Soc., (1962), pp. 2518–2521.
Brown; Australian J. Chem., vol. 8, pp. 121–124, (1955).
Brown et al.; Aust. J. Chem., vol. 8, pp. 348–377, (1954).

*Primary Examiner*—Mary C. Lee
*Attorney, Agent, or Firm*—Gerald D. Sharkin; Richard E. Vila

[57] ABSTRACT

Disclosed are compounds which are 4-hydroxy-2-quinolinone-3-carboxylic acid esters, e.g., 1-methyl-4-hydroxy-2-quinolinone-3-carboxylic acid ethyl ester, useful as anti-allergic agents and intermediates for 1-alkyl-4-alkoxy-quinolin-2(1H)-ones, and prepared by reacting an isatoic anhydride with an alkali metal salt of a malonic ester.

42 Claims, No Drawings

4-HYDROXY-2-QUINOLINONE-3-CARBOXYLIC ACID ESTERS

This is a division of application Ser. No. 807,898 filed June 20, 1977 now U.S. Pat. No. 4,190,659, which in turn is a continuation-in-part of Ser. No. 662,148, filed Feb. 27, 1976, now abandoned, which in turn is a continuation-in-part of Ser. No. 557,984, filed Mar. 12, 1975, now abandoned, which in turn is a division of Ser. No. 454,070, filed Mar. 25, 1974, now abandoned which in turn is a continuation-in-part of Ser. No. 303,099, filed Nov. 2, 1972 and of Ser. No. 392,082, filed Aug. 27, 1973, now both abandoned.

DISCLOSURE OF THE INVENTION

The present invention relates to chemical compounds and their use as pharmaceutical agents and intermediates, and more particularly to compounds which are 4-hydroxy-2-quinolinone-3-carboxylic acid esters which are useful as anti-allergic agents and as intermediates for 1-alkyl-4-alkoxyquinolin-2(1H)-ones.

In my earlier prior applications above-identified, there is disclosed, inter alia, compounds having CNS depressant activity and represented by the following structural formula I:

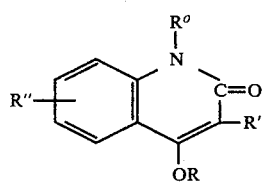

wherein
$R^o$ is alkyl of 1 to 6 carbon atoms,
R is alkyl of 1 to 8 carbon atoms,
R' is hydrogen or alkyl of 1 to 6 carbon atoms, and
R" is hydrogen, halo of atomic weight of from 18 to 80, i.e., fluoro, chloro or bromo or alkoxy of 1 to 4 carbon atoms.

The compounds I may be prepared in a Step A reaction by reacting a compound of the formula II:

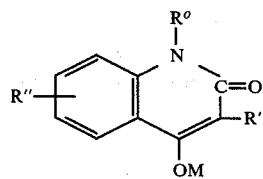

wherein $R^o$, R' and R" are as defined and M is hydrogen or an alkali metal, with a compound of the formula III:

RX      III wherein R is as defined and X is chloro, bromo or iodo or a radical of the formula IIIa:

BO—      IIIa in which B is methanesulfonyl, benzenesulfonyl or p-toluenesulfonyl.

The preparation of compounds I by the reaction of Step A may be suitably carried out at temperatures of from 0° C. to 120° C., preferably 10° C. to 40° C. The reaction may be carried out in absence of added solvent when III is liquid but is preferably effected with an inert solvent of conventional type such as dioxane, dimethylformamide and dimethylacetamide. The compounds of the formula II in which M is an alkali metal are preferably employed and are formed in a conventional manner by reacting a compound II in which M is hydrogen with a strong base such as an alkali metal hydride, an alkali metal hydroxide or alkali metal carbonate, preferably sodium hydride. When Step A is carried out employing a compound II in which M is hydrogen it is desirable to effect the reaction in the presence of strong base such as an alkali metal hydride, e.g., sodium hydride, or an alkali metal carbonate, e.g., potassium carbonate, and preferably at temperatures of from 10° C. to 80° C. The reaction product of the formula I may be recovered from the reaction mixture of Step A by working up by established procedures.

The compounds of the formula I may also be prepared in process B by reacting a compound of the formula IV:

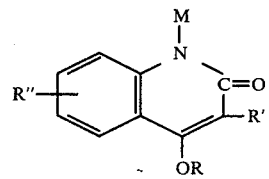

wherein R, R', R" and M are as above defined, with a compound of the formula V:

$R^o X$      V wherein $R^o$ and X are as defined above.

The preparation of compounds I by the reaction of process B may be suitably carried out at temperatures of from 0° C. to 120° C., preferably 10° C. to 40° C. The reaction may be carried out in absence of added solvent when V is liquid but is preferably effected with an inert solvent of conventional type such as dioxane, dimethylformamide and dimethylacetamide. The compounds of the formula IV in which M is an alkali metal are preferably employed and are formed in a conventional manner by reacting a compound IV in which M is hydrogen with a strong base such as an alkali metal hydride, an alkali metal hydroxide or alkali metal carbonate, preferably sodium hydride, at temperatures of from 0° C. to 120° C., preferably 10° C. to 80° C. When process B is carried out employing a compound IV in which M is hydrogen it is effected in the presence of a strong base such as an alkali metal hydride or carbonate, e.g., sodium hydride or potassium carbonate, and at temperatures of from 0° C. to 120° C., preferably 10° C. to 80° C. The reaction product of the formula I may be recovered from the reaction mixture of process B by working up by established procedures.

The compounds of the formula I in which R and $R^o$ are the same may be also prepared in process C by reacting a compound of the formula VI:

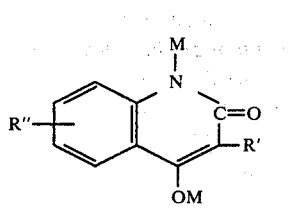

wherein R', R" and M are as above defined, with a compound of the formula V, given above.

Process C is carried out analogously to processes A and B employing at least about the theoretical amount of the compound of formula V to complete the reaction, i.e., at least 2 mols of compound V per mol of compound VI. When M is hydrogen it is preferable to employ temperatures of from 10° C. to 80° C. The compounds of the formula VI in which M is an alkali metal are formed in a conventional manner employing at least about the theoretical amount of an alkali metal hydride or the like, and at temperatures of from 0° C. to 120° C., preferably 10° C. to 80° C. In general, it is preferred to employ an excess of both the compound V and the base when preparing compounds I and an excess of alkali metal hydride or other suitable base when preparing the compounds of the formula VI in which M is an alkali metal.

The compounds of the formula II in which M is hydrogen are also either known or may be prepared from known materials by known procedures. For example, in U.S. Pat. No. 3,133,928 said compounds are disclosed and depicted in their alternative or tautomeric form having the structural formula IIa:

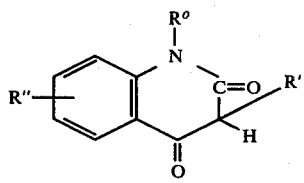

in which $R^o$, R' and R: are as above defined.

A procedure discovered for the preparation of the compounds of the formula II and preferred for preparation of certain such compounds, for example, those in which R' is alkyl, involves the reaction of a compound of the formula VII:

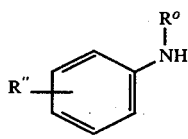

in which $R^o$ and R: are as above defined, with a compound of the formula VIII:

in which R' is as above defined and each R''' is alkyl of 1 to 4 carbon atoms.

The reaction of a compound VII with a compound VIII may be conveniently carried out in the presence or absence of a solvent at temperatures in the range of from 120° C. to 280° C., preferably in the absence of added solvents at temperatures of from 150° C. to 280° C., more preferably 200° C. to 250° C. Reaction times may vary fairly widely from say 1 hour to 50 hours, more typically 5 to 30 hours. The reaction of a compound VIII in which each R''' is ethyl and R' is butyl with a compound VII in which R' is methyl and R" is hydrogen has been effected satisfactorily at 220° C. over an 18 hour period. In general, the preferred compounds of the formula VIII are those in which each R''' is ethyl. The reaction product of the formula II may be recovered from the reaction mixture by working up by established procedures. The compounds of the formula VII and VIII are either known or may be prepared from known materials by conventional procedures.

The compounds of the formula IV employed in process B may be prepared by subjecting a compound of the formula IVa

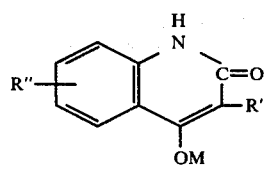

wherein R', R" and M are as defined, to reaction analogously to that of processes A, B and C as described above using controls to avoid any substantial alkylation of the 1-position of said compound IVa. Such control may be effected in the reaction in which the strong base is employed by:

(1) employing no more than about the theoretical amount of sodium hydride or other base used in the reaction, or (2), by employing a base to compound IVa mol ratio of about 1.5 to 1 or more and temperatures within the range of from 0° C. to 40° C., preferably 15° C. to 30° C., with the time and temperature of the reaction being regulated inversely with the mol ratio of base to compound IVa. In general, the mol ratio of base relative to the compound IVa is desirably no more than 3.1. Preferably, the ratio is about 1:1 and the temperature from 15° C. to 30° C.

The compound of the formulae IV and IVa in which M is hydrogen are either known or may be prepared from material by the known procedures.

The compound of the formula IIaa:

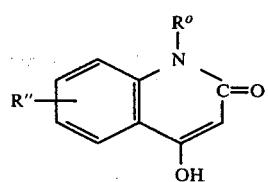

in which $R^o$ and R" are as defined above, may also be produced by hydrolysis and decarboxylation of a compound of formula IX:

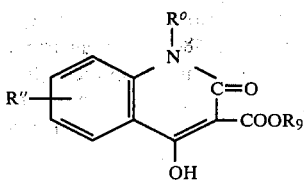

in which $R^o$ and $R''$ are as defined above, and $R_9$ is alkyl of 1 to 4 carbon atoms.

The hydrolysis may suitably be effected in the presence of a strong base, e.g., sodium hydroxide in an aqueous medium, e.g., water or aqueous ethanol, and at a temperature of from 40° C. to 150° C., preferably 80° C. to 120° C. The mixture may suitably then be acidified with, for example hydrochloric acid, and at a temperature of from 0° C. to 150° C., preferably 10° C. to 50° C., whereupon the free acid decarboxylates to yield the desired product. Where $R_9$ signifies t-butyl, the process is more suitably effected at a temperature of from 80° C. to 250° C., preferably 130° C. to 200° C. and in the presence or absence of an added solvent, such as a hydrocarbon or chlorinated hydrocarbon solvent.

The resulting compounds of formula IIaa may be isolated and purified using conventional techniques.

The compounds of formula IX are novel and may be produced by reacting a compound of formula X:

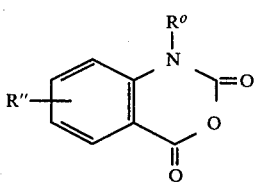

in which $R^o$ and $R''$ are as defined above, with a compound of formula XI:

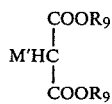

in which $R_9$ is as defined above, and

M' signifies an alkali metal.

The process is suitably carried out in an inert organic solvent, e.g., dimethyl acetamide, and at a temperature of from 0° C. to 150° C., preferably 60° C. to 120° C. followed, if necessary, by neutral or acid hydrolysis to obtain the desired compound IX from any 4-alkali metal salt thereof initially produced.

The compounds of formula XI may be produced from the corresponding dialkyl malonates by reaction with a strong alkali metal base, e.g., sodium hydride, and in an inert organic solvent, e.g., dimethyl acetamide.

The resulting compounds of formula IX may be isolated and purified using conventional techniques.

The compounds of formula X are either known or may be produced in conventional manner from available materials.

The compounds of the formula I are useful because they possess pharmacological activity in animals. In general, the compounds I effect a depression of the central nervous system and are useful as minor tranquilizers as indicated by a CNS depressant (docility) effect in behavior tests in mice (10–200 mg./kg.) and/or by an inhibition of chemically induced seizures in mice on intraperitoneal administration (10–200 mg./kg.) using 50 mg./kg. of N-sulfamoylazepine to induce seizures. Many of the compounds I such as those of Examples 4a, 4b, 4r, 4d, 4e and 4f hereinafter, also effect a reinduction of hexobarbital anesthesia in mice (10–200 mg./kg. Certain of the compounds I such as those of Examples 1, 3 and 4g hereinafter, in addition to all the above indications, provide responses indicative of a spectrum of tranquillizer activity having a muscle relaxant component as indicated by a neurological deficit and muscle relaxation in the "rotarod test" in mice on administration intraperitoneally (10–150 mg./kg.) essentially according to the method of Dunham et al., J. Am. Pharm. Assoc. 45:208, 1957, and/or a depression of spiral reflexes in anesthetized male cats on intravenous administration (0.5–20 mg./kg.) as determined by measuring flexor and patellar responses using force displacement transducers. The preferred compound which is 1-methyl-4-butoxyquinolin-2(1H)-one also inhibits aggression in the shocked-induced fighting mice test on administration intraperitoneally (20–100 mg./kg.).

For the above-mentioned usage, the dosage administered will of course vary depending upon known factors such as the compound used, mode of administration and therapy desired. However, in general, satisfactory results for the above usage may be obtained on administration of a compound I at a daily dose of from about 1.0 to 200 milligrams per kilogram of body weight, preferably given orally and in divided doses 2 to 4 times a day or in sustained release form. For larger mammals the administration of from 60 milligrams to 2000 milligrams of the compound per day provides satisfactory results and dosage forms suitable for internal administration comprise from about 15 milligrams to about 1000 milligrams of the compound in admixture with a solid or liquid pharmaceutical carrier.

It has now been found that the compounds IX, above disclosed, form a part of a larger series of compounds having pharmacological activity, in particular antiallergic activity, said series being represented structurally by the formula $IX_p$:

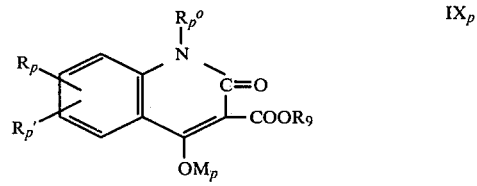

wherein $R_9$ is as above defined, and wherein $R_p{}^o$ is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

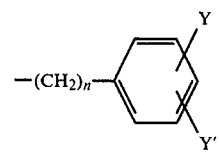

$M_p$ is hydrogen or a pharmaceutically acceptable cation, n is 0 or 1,

Y and Y' are independently hydrogen, halo of atomic weight of from 18 to 80, i.e., fluoro, chloro or bromo, alkyl of 1 to 3 carbon atoms, alkoxy of 1 to 3 carbon atoms, trifluoromethyl or nitro, with the proviso that only one of Y and Y' can be from the group consisting of nitro and trifluoromethyl, and $R_p$ and $R_p'$ are independently hydrogen, halo of atomic weight of from 18 to 80, i.e., fluoro, chloro or bromo, alkyl of 1 to 4 carbon atoms, alkoxy of 1 to 4 carbon atoms, nitro or trifluoromethyl, or $R_p$ and $R_p'$ together form 6,7-methylenedioxy, with the proviso that only one of $R_p$ and $R_p'$ can be from the group consisting of nitro and trifluoromethyl, with the further proviso that the unsaturation in any alkenyl or alkynyl is on other than the alpha carbon atom.

The compounds of the $IX_p$ in which M is hydrogen may be prepared by reacting a compound of the formula $X_p$:

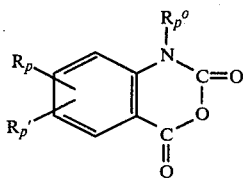

wherein $R_p^o$, $R_p$ and $R_p'$ are as above defined, with a compound of the formula XI:

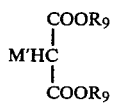

wherein $R_9$ and M' are as above defined, in the manner and under the condition hereinbefore described for the preparation of compounds IX from compound X and XI.

The comounds $IX_p$ in which $M_p$ is a pharmaceutically acceptable cation, e.g., lithium, sodium, potassium, ammonium, etc., may be prepared from the compound $IX_p$ in which $M_p$ is hydrogen by procedures well known in the art, e.g., by treating with a base such as dilute aqueous sodium hydroxide in a water miscible solvent.

The compounds of the formula $X_p$ and XI employed in the preparation of compound $IX_p$ are either known or may be produced in conventional manner from known materials, or as described herein.

The compound 4-methoxy-2-quinolinone-3-carboxylic acid ethyl ester is known from McCorkindale, Tetrahedron, 1961, Vol. 14, pp. 223–229, but to my knowledge has not been associated with any useful pharmacological activity. Also, Coutts et al., J. Chem. Soc. 1962, 2518–21, disclose the compound 4-hydroxy-2-quinolinone-3-carboxylic acid ethyl ester, but without the association of any useful pharmacological activity. Similarly, Brown, Australian J. Chem. 8, 121–4 (1955), disclose various N-unsubstituted polyalkoxy-4-hydroxy-2-quinolinone-3-carboxylic acid esters, eg. 6,7-dimethoxy-4-hydroxy-2-quinolinone-carboxylic acid methyl ester.

In addition to the novel compounds IX which also have particular use as intermediates for the compounds I, novel subgroupings within the scope of the compounds $IX_p$ provided by this invention and disclosed as of particular interest as anti-allergic agents in my aforementioned Ser. No. 662,148, now abandoned, are those in which $R_p$ and $R_p'$ are other than methylenedioxy and $R_p^o$ is: (a) alkenyl of 3 to 6 carbon atoms; (b) alkynyl of 3 to 6 carbon atoms; (c) cycloalkyl of 3 to 6 carbon atoms; (d) cycloalkylalkyl in which the cycloalkyl portion is of 3 to 6 carbon atoms and the alkyl portion is 1 or 2 carbon atoms; (e) Y,Y'-substituted phenyl wherein Y and Y' are as above defined: and (f) Y,Y'-substituted benzyl wherein Y and Y' are as above defined. Also of particular interest are the compounds of the formula $IX_p$ in which $R_p^o$ is hydrogen, $R_p$ is hydrogen, fluoro, chloro, bromo, alkyl of 1 to 4 carbon atoms or alkoxy of 1 to 4 carbon atoms and $R_p'$ is fluoro, chloro, bromo, alkyl of 1 to 4 carbon atoms or alkoxy of 1 to 4 carbon atoms. Similarly of particular interest are the compounds $IX_p$ in which $R_p^o$ is alkyl and $R_p$ and $R_p'$ are independently hydrogen, fluoro, chloro, bromo, alkyl of 1 to 4 carbon atoms or alkoxy of 1 to 4 carbon atoms.

Generally preferred compounds $IX_p$ ($R_p$ and $R_p'$ being other than methylenedioxy) are those having one or both, particularly both, of the features: (a) $R_p^o$ being hydrogen, alkyl or alkenyl, more preferably alkyl or alkenyl, and most preferably allyl; and (b) $R_p$ and $R_p'$ both being alkoxy, more preferably representing 6,7-dialkoxy, and most preferably representing 6,7-dimethoxy. Accordingly, representative additional novel subgroupings provided by the invention include those in which $R_p^o$ is alkyl or alkenyl, particularly allyl, and $R_p$ and $R_p'$ represent dialkoxy, more preferably 6,7-dialkoxy, and more preferably 6,7-dimethoxy.

further novel subgrouping provided by this invention are those compounds $IX_p$ in which $R_p$ and $R_p'$ together form 6,7-methylenedioxy, and the preferred significances of $R_p^o$ in such compounds are alkyl and alkenyl, more preferably allyl.

The compounds of formula $IX_p$ are useful because they possess pharmacological activity in animals. In particular they possess disodium chromoglycate (DSCG)-like activity, in particular histamine release inhibiting activity, and are therefore useful in the treatment of allergic conditions, such as allergic asthma, as indicated in the passive cutaneous anaphylaxis test in the rat. Female rats (180–200 g) are sensitised by subcutaneous administration of 1 mg. of egg albumin (Merck Nr. 967) and 200 mg of Al(OH)$_3$ dissolved in 1 ml of physiological saline and 0.5 ml of Haemophiluspertussis vaccine (Schweizerisches Serum and Impfinstitut, Bern; Nr. 115 325; $4 \times 10^{10}$ organism/ml) intraperitoneally. Fourteen days later, the animals are exsanguinated, the blood centrifuged, the serum collected and deep frozen. The serum thus obtained (anti-serum) is injected intradermally (0.1 ml of a 1:200 diluted serum per injection site) at four sites on the backs of untreated, female rats. Twenty-four hours later each rat is administered 0.1 to 5.6 mg/kg i.v. or 0.1 to 100 mg/kg p.o. of the test compound, and either immediately or 5 to 30 minutes afterwards, in the case of intravenous administration, or 15 or 60 minutes afterwards, in the case of oral administration, afterwards egg albumin (5 mg/ml i.v.) dissolved in physiological saline containing 0.25% Evans Blue dye (Merck Nr. 3169). The egg albumin elicits a cutaneous anaphylactic reaction, the intensity of which is proportional to the extent to which the Evans Blue dye diffuses into the tissue surrounding each of the four sensitisation sites. Thirty minutes after the administration of the egg albumin, the rats are killed with ether, the underside of the skin of the back of each animal is exposed and the diameter of the areas of blue dye surrounding each of the four sensitisation sites are measured. Each dose of test compounds is investigated in between four and six rats and the mean diameter compared with the mean value obtained in four solvent-treated control rats.

The percentage inhibition is taken as the percentage of the mean diameter in the test animals relative to the mean diameter in the controls.

The DSCG-like activity, in particular histamine release inhibiting activity, can be confirmed by inhibition of histamine release in the rat peritoneal mast cell test, basically as described by Kusner et al., J. Pharmacol. Exp. Therap. 184, 41–46 (1973), with the following modification: after sedimentation of the mast cells by centrifugation at $350 \times g$ and 4° C., the sediments are taken up in 1 ml of Hank's balanced salt solution (HBSS) (buffered to a pH of 6.9) and pooled. The resulting suspension is centrifuged, washed again with HBSS and sedimented. The thus purified mast cells are prepared as 2 ml suspensions in HBSS. To these are added either 2 ml of HBSS, to determine the spontaneous histamine release, or 2 ml of HBSS and 2.24 µg of compound 48/80 (N-methylhomoanisylamineformaldehyde condensate; a histamine liberator from Burroughs Wellcome and Co. Inc., Tuckahoe, N.Y. USA), to determine the 48/80 induced histamine release, or 2 ml of HBSS with 2.24 µg of 48/80 and from 18 to 180 µg/ml of the test compound, to determine the 48/80 induced histamine release in the presence of the test compound.

The 48/80 induced histamine release minus the spontaneous histamine release is taken as 100% histamine release. The 48/80 induced histamine release in the presence of the test compound minus the spontaneous histamine release is then compared with the 100% value to determine the percentage inhibition by the test compound. [The histamine determination is effected in conventional manner, for example, as described in the above-mentioned Kuzner et al. article, or in Kusner and Herzig, Advances in Automated Analysis, 429 (1971)].

For the above-mentioned anti-allergic use, the dosage administered will, of course, vary depending on the compound employed, mode of administration and treatment desired. However, satisfactory results are generally obtained on the administration of compounds $IX_p$ at a daily dosage of from about 0.3 to 100 mg/kg of animal body weight, conveniently given in divided doses two to four times daily, or in sustained release form. For he larger mammals, the total daily dosage is in the range of from about 20 to 800 mg of the compound admixed with a solid or liquid pharmaceutical carrier, and divided dosage forms comprise 5 to 400 milligrams of the compound in admixture with a solid or liquid pharmaceutical carrier. As will be appreciated by those skilled in the art, the treatment of allergic conditions according to the invention is based on histamine release inhibition activity and is therefore essentially symptomatic. The ability to employ such compounds in the prophylactic treatment of such allergic conditions (as evident from its DSCG-like activity) is a desirable features of such compounds. However, the good oral activity relative to DSCG is a further feature.

A representative formulation for administration 2 to 4 times a day for prophylactic treatment of allergic asthma is a capsule prepared by standard techniques to contain the following:

| Ingredient | Weight (mg) |
|---|---|
| N-allyl-6,7-dimethoxy-4-hydroxy-2-quinolinone-3-carvoxylic acid ethyl ester | 10 |
| Kaolin | 210 |

The following examples are given for purposes of illustration only.

EXAMPLE 1

1-Methyl-4-butoxyquinolin-2(1H)-one

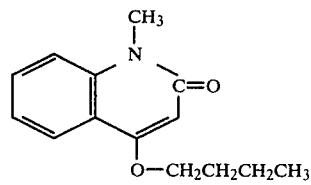

To a solution of 10.0 g. of 1-methyl-4-hydroxyquinolin-2(1H)-one in 150 ml. of dimethylformamide is added 2.4 g. of pentane washed with sodium hydride and the resulting mixture stirred for 2 hours at room temperature. There is then added 10.6 g. of n-butyl iodide and the resulting mixture is stirred for 24 hours at room temperature. The reaction mixture is then poured onto 1.3 liters of cold water, extracted with ethyl acetate, washed 3 times with water, dried, charcoaled, filtered and evaporated in vacuo. The resulting oil is dissolved in 120 ml. of ether and cooled in an acetone/dry ice bath to crystallize solids which are filtered off and washed with cold ether to obtain 1-methyl-4-butoxyquinolin-2(1H)-one, m.p. 77°–80° C.

EXAMPLE 2

1-Methyl-4-ethoxyquinolin-2(1H)-one (Process 2)

Step A: Preparation of 4-ethoxyquinolin-2(1H)-one.

To a suspension of 6 g. of quinoline-2,4-dione in 50 ml. of dimethylacetamide is added 1.6 g. of sodium hydride (56% in mineral oil, pentane washed). The mixture is then stirred at room temperature for 90 minutes and 6 g. of ethyliodide is added and the resulting mixture is heated briefly at 35° C. followed by stirring at ambient temperature for 18 hours. The precipitate which forms is recovered by filtering and the filtrate is poured into 200 ml. of water and the resulting precipitate also recovered by filtering and dried. The two filter cakes above obtained are combined and crystallized from methanol to obtain 4-ethoxyquinolin-2(1H)-one, m.p. 223°–226° C.

Step B: Preparation of 1-methyl-4-ethoxyquinolin-2(1H)-one.

To a suspension of 1.9 g. of 4-ethoxyquinolin-2(1H)-one in 40 ml. of dimethylacetamide is added 0.42 g. of sodium hydride (56% in mineral oil, pentane washed), and the resulting mixture is heated at 60° C. for one hour. The mixture is filtered (while excluding moisture), cooled and there is then added 1.5 g. of methyliodide followed by stirring for 2 hours at ambient temperatures. The resulting mixture is poured into 200 ml. of cold water and the resulting slurry extracted 3 times each with 100 ml. of ethyl acetate. The combined organic extracts are washed with water and saturated sodium chloride solution, dried and evaporated in vacuo. The residue is crystallized from ether to obtain 1-methyl-4-ethoxyquinolin-2(1H)-one, m.p. 80°–82° C.

EXAMPLE 3

Preparation by Process 3 of 1-Butyl-4-butoxyquinolin-2(1H)-one.

To a suspension of 10 g. of 4-hydroxyquinolin-2(1H)-one in 100 ml. of dimethylacetamide is added in portions 5.4 g. of sodium hydride (57% in mineral oil, pentane washed) and the mixture then stirred for one hour at room temperature. There is then added dropwise 24 g. of n-butyl iodide and the mixture is stirred for 3 hours at ambient temperatures. The resulting mixture is poured into water, extracted with ethyl acetate, the organic phase washed with water and saturated sodium chloride solution, dried and evaporated in vacuo. The residue is dissolved in chloroform and subjected to column chromatography (silica gel) and thin layer chromatography employing a s-lution of 5% ethanol and 95% chloroform as solvent. The product ($R_f$ 0.75) obtained subsequent to the first eluted product ($R_f$ 0.85) is purified by distillation under high vacuum (142°–148° C. @ 0.1 mm/Hg.) and crystallized from ether to obtain 1-butyl-4-4butoxyquinolin-2(1H)-one, m.p. 50°–52° C.

EXAMPLE 4

Following the procedure of Examples 1 and 2, the following additional compounds of the invention are prepared:
(a) 1-methyl-4-methoxyquinolin-2(1H)-one, m.p. 95°–100° C.
(b) 1-methyl-4-hexoxyquinolin-2(1H)-one, m.p. 66°–69° C.
(c) 1-methyl-4-sec-butoxyquinolin-2(1H)-one, as an oil.
(d) 1-methyl-4-isobutoxyquinolin-2(1H)-one, m.p. 85°–87° C.
(e) 1-butyl-4-hexoxyquinolin-2(1H)-one, m.p. 45°–48° C.
(f) 1-ethyl-4-hexoxyquinolin-2(1H)-one, m.p. 56°–58° C.
(g) 1-methyl-4-pentoxyquinolin-2(1H)-one, m.p. 62°–65° C.
(h) 1-methyl-4-butoxy-3-butylquinolin-2(1H)-one, as an oil.
(i) 1-methyl-2-ethoxyquinolin-2(1H)-one, m.p. 78°–81° C.
(j) 1-butyl-4-pentoxyquinolin-2(1H)-one, m.p. 45°–48° C.
(k) 1-methyl-4-propoxyquinolin-2(1H)-one, m.p. 83°–85° C.
(l) 7-chloro-1-butyl-4-butoxyquinolin-2(1H)-one, m.p. 98°–100° C.
(m) 1-hexyl-4-hexoxyquinolin-2(1H)-one, m.p. 54°–56° C.
(n) 6-methoxy-1-methyl-4-butoxyquinolin-2(1H)-one, m.p. 99°–102° C.
(o) 6-chloro-1-methyl-4-butoxyquinolin-2(1H)-one, m.p. 140°–143° C.
(p) 7-chloro-1-butyl-4-hexoxyquinolin-2(1H)-one, m.p. 95°–98° C.
(q) 1-methyl-4-heptoxyquinolin-2(1H)-one, m.p. 39°–41° C.
(r) 1-methyl-4(2-pentyl)-quinolin-2(1H)-one, as an oil.
(s) 1-methyl-4-octoxyquinolin-2(1H)-one, m.p. 67°–69° C.

EXAMPLE 5

Following the procedure of Example 3, the following compounds are prepared:
(a) 1-methyl-4-methoxyquinolin-2(1H)-one, m.p. 95°–100° C.
(b) 7-chloro-1-butyl-4-butoxyquinolin-2(1H)-one, m.p. 98°–100° C.
(c) 1-hexyl-4-hexoxyquinolin-2(1H)-one, m.p. 54°–56° C.

EXAMPLE 6

N-Butyl-4-butoxyquinolin-2(1H)-one (a) N-Butyl-4-hydroxy-2-quinolinone-3-carboxylic acid ethyl ester.

A solution of 25 g. of N-butylisatoic anhydride in 100 ml. of dimethylacetamide is added, dropwise, to a solution of sodio-diethyl malonate (prepard by reacting 20 g. of diethyl malonate in 100 ml. of dimethylacetamide with 5.3 g. of sodium hydride (57% in mineral oil)—first at room temperature and then briefly at 120° C.). The resulting mixture is heated at 120° C. for 16 hours. The dimethyl acetamide is evaporated off, water is added and the mixture extracted with ethyl acetate. The organic phase is extracted twice with water and then with saturated sodium chloride solution, followed by drying over sodium sulphate and evaporation in vacuo. The residue is dissolved in 150 ml. of methylene chloride and 100 ml. of diethyl ether is added. The precipitate is filtered off and the filtrate is evaporated and eluted through a silica column with a mixture of 98% chloroform and 2% methanol to yield an oil which crystallizes on standing. The crystals are filtered off, after addition of pentane to yield the heading compound, m.p. 54°–55° C.

(b) N-Butyl-4-hydroxyquinoline-2(1H)-one.

8.8 g. of N-butyl-4-hydroxy-2-quinolin-3-carboxylic acid ethyl ester is refluxed with 100 ml. of 2 N sodium hydroxide solution for 24 hours. The resulting solution is heated with charcoal, acidified with 2 N HCl and the precipitate filtered off, washed with water dried and recrystallized from methanol to obtain the heading compound, m.p. 211°–213° C.

(c) 1-Butyl-4-butoxyquinolin-2(1H)-one.

In manner analogous to Example 1, employing an approximately equivalent amount of the compound of step (b), above, in place of the 1-methyl-4-hydroxyquinolin-2(1H)-one, the heading compound, m.p. 50°–52° C. is obtained.

EXAMPLE 7

In manner analogous to Example 6a, employing appropriate starting materials in approximately equivalent amounts, the following compounds may be obtained:
(A) N-hexyl-4-hydroxy-2-quinolinone-3-carboxylic acid ethyl ester, m.p. 64°–66° C.,
(B) N-ethyl-4-hydroxy-2-quinolinone-3-carboxylic acid ethyl ester, m.p. 68°–71° C.,
(C) N-butyl-7-chloro-4-hydroxy-2-quinolinone-3-carboxylic acid ethyl ester, m.p. 54°–55° C.,
(D) N-methyl-6-methoxy-4-hydroxy-2-quinolinone-3-carboxylic acid ethyl ester, m.p. 130° to 133° C.
(E) N-methyl-6-chloro-4-hydroxy-2-quinolinone-3-carboxylic acid ethyl ester, m.p. 132°–135° C.
(F) N-methyl-4-hydroxy-2-quinolinone-3-carboxylic acid ethyl ester, m.p. 100°–102° C.

(G) 6-methyl-4-hydroxy-2-quinolinone-3-carboxylic acid ethyl ester.
(H) N-allyl-4-hydroxy-2-quinolinone-3-carboxylic acid ethyl ester, m.p. 88°–91° C.
(I) N-allyl-6,7-dimethoxy-4-hydroxy-2-quinolinone-3-carboxylic acid ethyl ester, m.p. 165°–166° C.
(J) 6,7-dimethoxy-4-hydroxy-2-quinolinone-3-carboxylic acid ethyl ester.
(K) 6-chloro-4-hydroxy-2-quinolinone-3-carboxylic acid ethyl ester.
(L) N-cyclopentyl-4-hydroxy-2-quinolinone-3-carboxylic acid ethyl ester.
(M) N-cyclopropylmethyl-4-hydroxy-2-quinolinone-3-carboxylic acid ethyl ester.
(N) N-(o-nitrobenzyl)-4-hydroxy-2-quinolinone-3-carboxylic acid ethyl ester, m.p. 148°–151° C.
(O) N-propargyl-4-hydroxy-2-quinolinone-3-carboxylic acid ethyl ester, m.p. 171°–174° C.
(P) N-(p-fluorobenzyl)-4-hydroxy-2-quinolinone-3-carboxylic acid ethyl ester, 126°–129° C.
(Q) N-phenyl-4-hydroxy-2-quinolinone-3-carboxylic acid ethyl ester, 180°–183° C.
(R) N-methyl-6,7-dimethoxy-4-hydroxy-2-quinolinone-3-carboxylic acid ethyl ester, m.p. 216°–219° C.
(S) N-(2-butynyl)-6,7-dimethoxy-4-hydroxy-2-quinolinone-3-carboxylic acid ethyl ester, m.p. 244°–246° C.
(T) N-(2-methyl-3-propenyl)-6,7-dimethoxy-4-hydroxy-2-quinolinone-3-carboxylic acid ethyl ester, m.p. 163°–164° C.
(U) N-propyl-6,7-dimethoxy-4-hydroxy-2-quinolinone-3-carboxylic acid ethyl ester, m.p. 166°–169° C.
(V) N-cyclopropylmethyl-6,7-dimethoxy-4-hydroxy-2-quinolinone-3-carboxylic acid ethyl ester, m.p. 176°–178° C.
(W) N-allyl-6,7-dimethoxy-4-hydroxy-2-quinolinone-3-carboxylic acid n-butyl ester, m.p. 144°–147° C.
(X) N-(2-butenyl)-6,7-methoxy-4-hydroxy-2-quinolinone-3-carboxylic acid ethyl ester, m.p. 151°–154° C.
(Y) N-(3-butenyl)-6,7-dimethoxy-4-hydroxy-2-quinolinone-3-carboxylic acid ethyl ester, m.p. 193°–195° C.
(Z) N-allyl-6,7-dimethoxy-4-hydroxy-2-quinolinone-3-carboxylic acid t-butyl ester, m.p. 142°–144° C.
(Z-1) N-allyl-6,7-methylenedioxy-2-quinolinone-4-hydroxy-3-carboxylic acid ethyl ester, m.p. 147°–149° C.
(Z-2) N-allyl-6,7-dichloro-4-hydroxy-2-quinolinone-3-carboxylic acid ethyl ester, m.p. 146°–148° C.
(Z-3) N-allyl-6-methoxy-7-ethyl-4-hydroxy-2-quinolinone-3-carboxylic acid ethyl ester.
(Z-4) N-allyl-6-methoxy-7-methyl-4-hydroxy-2-quinolinone-3-carboxylic acid ethyl ester.
(Z-5) N-allyl-6,7-dimethyl-4-hydroxy-2-quinolinone-3-carboxylic acid ethyl ester.

Pharmaceutical compositions provided by the invention and useful for treating allergic conditions due to histamine release contain a compound of the formula $IX_p$ as active ingredient and one or more conventional pharmaceutically acceptable carriers, and such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositions including applicable unit dosage forms thereof may be prepared according to any method known in the art for the manufacture of pharmaceutical compositions. The compounds may also be administered by inhalation therapy techniques in compositions conventionally prepared and adapted for such procedures. In general, the compositions of the invention adapted for either oral, inhalation or parenteral administration may contain from 1% to 90% by total weight of active ingredient in combination with the carrier, more usually 3% to 70%. The preferred unit dosage forms are the essentially solid forms adapted for oral administration, e.g., tablets or capsules.

Another subgrouping of the compounds $IX_p$ of interest are those in which $R_p{}^o$ is allyl, $R_p$ is alkyl of 1 to 4 carbon atoms in the 7-position, preferably methyl or ethyl, and $R_p{}'$ is alkoxy of 1 or 2 carbon atoms in the 6-position, preferably methoxy.

What is claimed is:

1. A compound of the formula:

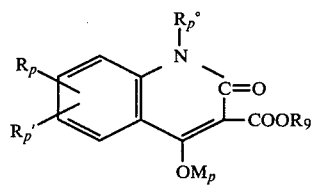

wherein $R_9$ is alkyl of 1 to 4 carbon atoms, wherein
$R_p{}^o$ is alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

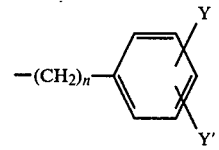

$M_p$ is hydrogen or a pharmaceutically acceptable cation, n is 0 or 1,

Y and Y' are independently hydrogen, fluoro, chloro, bromo, alkyl of 1 to 3 carbon atoms, alkoxy of 1 to 3 carbon atoms, trifluoromethyl or nitro with the proviso that only one of Y and Y' can be from the group of nitro and trifluoromethyl, and $R_p$ and $R_p{}'$ are independently hydrogen, fluoro, chloro, bromo, alkyl of 1 to 4 carbon atoms, alkoxy of 1 to 4 carbon atoms, nitro or trifluoromethyl, with the proviso that only one of $R_p$ and $R_p{}'$ can be from the group consisting of nitro and trifluoromethyl, with the further proviso that the unsaturation in any alkenyl or alkynyl is on other than the alpha carbon atom.

2. A compound of claim 1 in which $M_p$ is hydrogen.
3. A compound of claim 1 in which $R_p{}^o$ is alkenyl.
4. A compound of claim 1 in which $R_p{}^o$ is alkynyl.
5. A compound of claim 1 in which $R_p{}^o$ is cycloalkyl.
6. A compound of claim 1 in which $R_p{}^o$ is cycloalkylalkyl.
7. A compound of claim 1 in which $R_p{}^o$ is

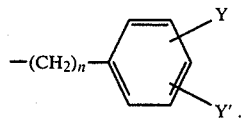

8. A compound of claim 7 in which n is 0.

9. A compound of claim 7 in which n is 1.

10. A compound of claim 1 in which $R_p$ and $R_p'$ are each alkoxy of 1 to 4 carbon atoms.

11. A compound of claim 10 in which $R_p$ and $R_p'$ represent 6,7-dialkoxy.

12. A compound of claim 11 in which $R_p$ and $R_p'$ represent 6,7-dimethoxy.

13. A compound of claim 12 in which $R_p{}^o$ is allyl.

14. The compound of claim 3 which is N-allyl-4-hydroxy-2-quinolinone-3-carboxylic acid ethyl ester.

15. The compound of claim 13 which is N-allyl-6,7-dimethoxy-4-hydroxy-2-quinolinone-3-carboxylic acid ethyl ester.

16. The compound of claim 9 which is N-(p-fluorobenzyl)-4-hydroxy-2-quinolinone-3-carboxylic acid ethyl ester.

17. The compound of claim 5 which is N-cyclopentyl-4-hydroxy-2-quinolinone-3-carboxylic acid ethyl ester.

18. The compound of claim 6 which is N-cyclopropylmethyl-4-hydroxy-2-quinolinone-3-carboxylic acid ethyl ester.

19. The compound of claim 4 which is N-propargyl-4-hydroxy-2-quinolinone-3-carboxylic acid ethyl ester.

20. The compound of claim 8 which is N-phenyl-4-hydroxy-2-quinolinone-3-carboxylic acid ethyl ester.

21. A compound of the formula:

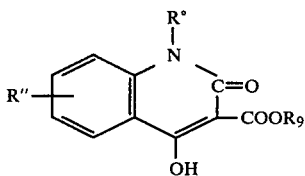

wherein
$R^o$ is alkyl of 1 to 6 carbon atoms,
$R''$ is hydrogen, fluoro, chloro, bromo or alkoxy of 1 to 4 carbon atoms, and
$R_9$ is alkyl of 1 to 4 carbon atoms.

22. The compound of claim 21 which is N-hexyl-4-hydroxy-2-quinolinone-3-carboxylic acid ethyl ester.

23. The compound of claim 21 which is N-ethyl-4-hydroxy-2-quinolinone-3-carboxylic acid ethyl ester.

24. The compound of claim 21 which is N-butyl-7-chloro-4-hydroxy-2-quinolinone-3-carboxylic acid ethyl ester.

25. The compound of claim 21 which is N-methyl-6-methoxy-4-hydroxy-2-quinolinone-3-carboxylic acid ethyl ester.

26. The compound of claim 21 which is N-methyl-6-chloro-4-hydroxy-2-quinolinone-3-carboxylic acid ethyl ester.

27. A compound of the formula:

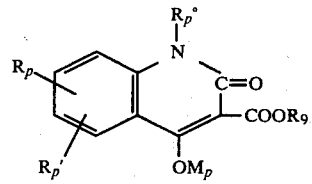

wherein $R_9$ is alkyl of 1 to 4 carbon atoms, wherein
$R_p{}^o$ is alkyl of 1 to 6 carbon atoms,
$M_p$ is hydrogen or a pharmaceutically acceptable cation, and
$R_p$ and $R_p'$ are independently alkoxy of 1 to 4 carbon atoms.

28. A compound of claim 27 in which $R_p$ and $R_p'$ represent 6,7-dialkoxy.

29. A compound of claim 28 in which $R_p$ and $R_p'$ represent 6,7-dimethoxy.

30. A compound of claim 29 in which $R_p{}^o$ is methyl.

31. The compound of claim 30 which is N-methyl-6,7-dimethoxy-4-hydroxy-2-quinolinone-3-carboxylic acid ethyl ester.

32. A compound of the formula:

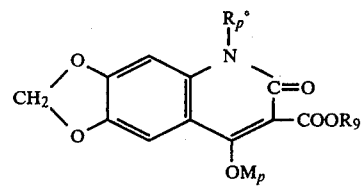

wherein $R_9$ is alkyl of 1 to 4 carbon atoms, wherein
$R_p{}^o$ is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

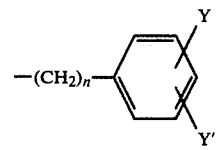

$M_p$ is hydrogen or a pharmaceutically acceptable cation,
n is 0 or 1, and
Y and Y' are independently hydrogen, fluoro, chloro, bromo, alkyl of 1 to 3 carbon atoms, alkoxy of 1 to 3 carbon atoms, trifluoromethyl or nitro, with the proviso that only one of Y and Y' can be from the group consisting of nitro and trifluoromethyl, with the further proviso that the unsaturation in any alkenyl or alkynyl is on other than the alpha carbon atom.

33. A compound of claim 32 in which $R_p{}^o$ is alkyl.

34. A compound of claim 32 in which $R_p{}^o$ is alkenyl.

35. A compound of claim 34 in which $R_p{}^o$ is allyl.

36. The compound of claim 35 which is N-allyl-6,7-methylenedioxy-4-hydroxy-2-quinolinone-3-carboxylic acid ethyl ester.

37. The compound of claim 13 which is N-allyl-6,7-dimethoxy-4-hydroxy-2-quinolinone-3-carboxylic acid n-butyl ester.

38. The compound of claim 13 which is N-allyl-6,7-dimethoxy-4-hydroxy-2-quinolinone-3-carboxylic acid t-butyl ester.

39. A compound of claim 3 in which $R_p^o$ is allyl.

40. A compound of claim 39 in which $R_p$ is alkyl of 1 to 4 carbon atoms in the 7-position and $R_p'$ is alkoxy of 1 to 2 carbon atoms in the b 6-position.

41. The compound of claim 40 which is N-allyl-6-methoxy-7-ethyl-4-hydroxy-2-quinolinone-3-carboxylic acid ethyl ester.

42. The compound of claim 40 which is N-allyl-6-methoxy-7-methyl-4-hydroxy-2-quinolinone-3-carboxylic acid ethyl ester.

* * * * *